US006455263B2

(12) United States Patent
Payan

(10) Patent No.: US 6,455,263 B2
(45) Date of Patent: *Sep. 24, 2002

(54) SMALL MOLECULE LIBRARY SCREENING USING FACS

(75) Inventor: Donald Payan, Hillsborough, CA (US)

(73) Assignee: Rigel Pharmaceuticals, Inc., South San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/047,119

(22) Filed: Mar. 24, 1998

(51) Int. Cl.[7] .................. G01N 33/53; G01N 33/543; G01N 21/76; C07K 16/00
(52) U.S. Cl. .................. 435/7.1; 435/7.2; 435/7.9; 435/DIG. 14; 435/DIG. 40; 435/DIG. 41; 436/518; 436/527; 436/531; 436/80; 436/172
(58) Field of Search .................. 435/7.1, 7.2, 7.21, 435/7.23, 7.24, 7.5, 7.72, 7.8, 7.9, 7.92, 7.93, 7.94, 7.4, DIG. 1, DIG. 2, DIG. 15, DIG. 17, DIG. 21, DIG. 40, DIG. 41, DIG. 14; 436/518, 527, 531, 86, 172

(56) References Cited

U.S. PATENT DOCUMENTS

| 5,639,603 A | | 6/1997 | Dower et al. | |
| 5,981,180 A | * | 11/1999 | Chandler et al. | 435/6 |

FOREIGN PATENT DOCUMENTS

| WO | 89/11101 | 11/1989 |
| WO | 93/02360 | 2/1993 |
| WO | 94/24314 | 10/1994 |
| WO | 95/12608 | 5/1995 |
| WO | 95/32425 | 11/1995 |
| WO | 96/16333 | 5/1996 |
| WO | 97/14028 | 4/1997 |

OTHER PUBLICATIONS

Stewart Carleton C (Methods in Immunology., vol. 33., Edited by Crissman. H A and Darzynkiewicz. Z., Academic Press. Inc., San Diego, California 92101., 1990., pp. 411–426.*

M. Adamczyk et al. (1997), "The Utility of Enzymes in Generating Molecular Diversity. Lipase Mediated Amidation of Polybenzyl Esters", *Biorganic & Medicinal Chemistry Letters* 7 (8):1027–1030.

S. Bass, et al. (1990), "Hormone Phage: An Enrichment Method for Variant Proteins with Altered Binding Properties", *Proteins: Structure, Function, and Genetics* 8:309–314.

A. Borchardt et al. (1994), "Synthetic Receptor Binding Elucidated with an Encoded Combinatorial Library", *J. Am. Chem. Soc.* 116:373–374.

R. Boyce et al. (1994) "Peptidosteriodal Receptors for Opioid Peptides. Sequence–Selective Binding Using a Synthetic Receptor Library", *J. Am. Chem. Soc.* 116:7955–7956.

J.A. Ellman (1996), "Design, Synthesis, and Evaluation of Small–Molecule Libraries", *Acc. Chem. Res.* 29:132–143.

M.A. Gallop et al. (1994), "Applications of Combinatorial Technologies to Drug Discovery. 1. Background and Peptide Combinatorial Libraries", *Journal of Medicinal Chemistry* 37(9):1233–1251.

M.A. Gallop et al. (1997), "New methods for analyzing compounds on polymeric supports", *Chemical Biology* 1:94–100.

C. Gennari et al. (1995), "Synthetic Receptors Based on Vinylogous Sulfonyl Peptides", *Agnew. Chem. Int. Ed. Engl.* 34(16):1765–1768.

E.M. Gordon et al. (1994), "Applications of Combinatorial Technologies to Drug Discovery. 2. Combinatorial Organic Synthesis, Library Screening Strategies, and Future Directions", *Journal of Medicinal Chemistry* 37(10):1385–1401.

E.M. Gordon et al. (1996), "Strategy and Tactics in Combinatorial Organic Synthesis. Applications to Drug Discovery", *Acc. Chem. Res.* 29:144–154.

E.M. Gordon et al. (1995), "Combinatorial Organic Synthesis: Applications to Drug Discovery", *European Journal of Medicinal Chemistry* 30:338–348.

C.P. Holmes et al. (1995), "Strategies for Combinatorial Organic Synthesis: Solution and Polymer–Supported Synthesis of 4–Thiazolidinones and 4–Metathiazanones Derived from Amino Acids", *J. Org. Chem.* 60:7328–7333.

D. Kahne et al (1988), "Hydrolysis of a Peptide Bond in Neutral Water", *J. Am. Chem. Soc.* 110:7529–7534.

A. Kassarjian et al. (1993) "Screening of Synthetic Peptide Libraries with Radiolabeled Acceptor Molecules", *Peptide Research* 6(3): 129–133.

D. Maclean et al. (1997), "Encoded combinatorial chemistry: Synthesis and screening of a library of highly functionalized pyrrolidines", *Proc. Natl. Acad. Sci. USA* 94:2805–2810

M.M Murphy et al. (1995), "Combinatorial Organic Synthesis of Highly Functionalized Pyrrolidines: Identification of a Potent Angiotensin Converting Enzyme Inhibitor from a Mercaptoacyl Proline Library", *J. Am. Chem. Soc.* 117:7029–7030.

(List continued on next page.)

Primary Examiner—Padmashri Ponnaluri
(74) Attorney, Agent, or Firm—Dorsey & Whitney LLP; Robin M. Silva, Esq.

(57) ABSTRACT

The present invention relates to methods of screening libraries of small molecules such as combinatorial chemical libraries of organic molecules, including peptides and other chemical libraries, for binding to target molecules, using fluoroscence-activated cell sorting (FACS) machines.

4 Claims, No Drawings

OTHER PUBLICATIONS

M.C. Needels et al. (1993), "Generation and screening of an oligonucleotide–encoded synthetic peptide library", *Proc. Natl. Acad. Sci. USA 90*:10700–10704.

H.P. Nestler et al. (1996), "Microautoradiographic Identification of Receptor–Ligand Interactions in Bead–Supported Combinatorial Libraries", *Biorganic & Medicinal Chemistry Letters 6*(12):1327–1330.

Z–J. Ni et al. (1996), "Encoded Combinatorial Chemistry: Binary Coding Using Chemically Robust Secondary Amine Tags", *Methods in Enzymology 267*:261–272.

Z–J. Ni et al. (1996), "Versatile Approach to Encoding Combinatorial Organic Syntheses Using Chemically Robust Secondary Amine Tags", *J. Med. Chem. 39*:1601–1608.

M.A. Gallop et al. (1994), "Generation of Binary–Encoded Combinatorial Libraries and Their Applicatons to Ligand Discovery", *Chemtracts—Organic Chemistry 7*(3)):172–178.

B. Ruhland et al. (1996), "Solid–Supported Combinatorial Synthesis of Structurally Divers β–Lactams", *J. Am. Chem. Soc. 118*:253–254.

W.C. Still (1996), "Discovery of Sequence–Selective Peptide Binding by Synthetic Receptors Using Encoded Combinatorial Libraries", *Acc. Chem. Res. 29*:155–163.

D. Vetter et al. (1995), "Strategies for the Synthesis and Screening of Glycoconjugates. 1. A Library of Glycosylamines", *Bioconjugate Chem. 6*:316–318.

D. Vetter et al. (1995), "Strategies for the Synthesis and Screening of Glycoconjugates. 2. Covalent Immobilization for Flow Cytometry", *Bioconjugate Chem.6*:319–322.

H. Wennemers et al. (1995), "Cyclooligomeric Receptors Based on Trimesic Acid and 1,2–Diamines. Minimal Structure for Sequence–Selective Peptide Binding", *J. Org. Chem. 60*:1108–1109.

* cited by examiner

SMALL MOLECULE LIBRARY SCREENING USING FACS

FIELD OF THE INVENTION

The present invention relates to methods of screening libraries of small molecules such as combinatorial chemical libraries of organic molecules, including peptides and other chemical libraries, for binding to target molecules, using fluoroscence-activated cell sorting (FACS) machines.

BACKGROUND OF THE INVENTION

Traditional approaches to identify and characterize new and useful drug candidates include the isolation of natural products or synthetic preparation, followed by testing against either known or unknown targets. See for example WO 94/24314, Gallop et al., J. Med. Chem. 37(9):1233 (1994); Gallop et al., J. Med. Chem. 37(10):1385 (1994); Ellman, Acc. Chem. Res. 29:132 (1996); Gordon et al., E. J. Med. Chem. 30:388s (1994); Gordon et al., Acc. Chem. Res. 29:144 (1996); WO 95/12608, all of which are incorporated by reference.

The screening of these libraries is done in a variety of ways. One approach involves attachment to beads and visualization with dyes; see Neslter et al., Bioorg. Med. Chem. Lett. 6(12):1327 (1996). Another approach has utilized beads and fluorescence activated cell sorting (FACS); see Needles et al., PNAS USA 90:10700 (1993), and Vetter et al., Bioconjugate Chem. 6:319 (1995).

Fluorescence activated cell sorting (FACS), also called flow cytometry, is used to sort individual cells on the basis of optical properties, including fluorescence. It is generally fast, and can result in screening large populations of cells in a relatively short period of time.

Accordingly, it is an object of the invention to provide methods for the rapid, accurate screening of candidate agents, particularly libraries of agents, using FACS methods.

SUMMARY OF THE INVENTION

In accordance with the objects outlined above, the present invention provides methods for screening candidate bioactive agents for binding to a target molecule. The methods comprise contacting a library of candidate bioactive agents covalently attached to a plurality of beads with at least a first population of first target molecules labeled with a first labeling moiety. A fluorescent second labeling moiety capable of binding to said first labeling moiety is then added, and the beads are sorted using a fluorescent activated cell sorter (FACS) machine to obtain a population of fluorescent beads and a population of non-fluorescent beads. The presence of at least one fluorescent bead is indicative that at least one candidate bioactive agent that binds to at least one target molecule.

In an additional aspect, the methods comprise contacting a library of candidate bioactive agents covalently attached to a plurality of beads with at least a first population of first target molecules comprising at least a first subpopulation and a second subpopulation. The first subpopulation is labeled with a first labeling moiety (and optionally with a third labeling moiety) and the second subpopulation is labeled with a second labeling moiety (and optionally with a fourth labelling moiety). The beads are then sorted using a fluorescent activated cell sorter (FACS) machine to obtain a population of fluorescent beads and a population of non-fluorescent beads, wherein the presence of at least one fluorescent bead is indicative that at least one candidate bioactive agent binds to at least one first target molecule.

In a further aspect, the methods comprise contacting a library of candidate bioactive agents covalently attached to a plurality of beads with at least a first population of first target molecules labeled with a first labeling moiety (and optionally a second labeling moiety), and sorting the beads using a fluorescent activated cell sorter (FACS) machine to obtain a population of fluorescent beads and a population of non-fluorescent beads. A competitor moiety known to bind to the first target is then added, and the beads are resorted by a FACS machine to produce a population of beads which are no longer fluorescent, wherein the presence of at least one bead which was fluorescent in step (c) but is no longer fluorescent in step (e) indicates that at least one candidate bioactive agent is a bioactive agent that binds to is said first target molecule.

In an additional aspect, the methods of the invention further comprise chemically modifying the candidate bioactive agents to form new candidate bioactive agents, which may then be rescreened using the methods of the invention.

DETAILED DESCRIPTION OF THE INVENTION

The present invention relates to methods of screening candidate agents for the capacity to bind to a target molecule. Generally speaking, a preferred embodiment of the invention is described as follows. Many synthetic reactions for small molecules (organic moieties, peptides, nucleic acids, etc.) are amenable to solid phase synthesis. Thus, solid phase synthesis may be done on support particles or beads that can be sorted by FACS machines. In this way, a library of beads containing a library of candidate bioactive agents can be made. The number of candidate bioactive agents can vary, as will the number of beads which contain a particular candidate agent.

Once generated, the library of beads is added to a population of target molecules for which an interaction is sought. The target molecules are labelled with a first labeling moiety, which can either be a fluorescent tag or a molecule to which a second label which is fluorescent can be added. Thus for example, the target molecule may be labeled either directly with a fluorescent tag, or with a hapten such as biotin, followed by treatment with a a fluorescently labeled second moiety such as streptavidin (or both). The latter technique may be particularly advantageous to "amplify" the fluorogenicity of the target, thus allowing smaller amounts of target to be used and/or detected. In either case the target molecule is ultimately fluorescent. The beads are added, and allowed to interact under conditions which will favor binding of a candidate bioactive agent and a target molecule. The beads are then subjected to sorting by FACS, which allows the beads with bound fluorescent targets, and thus bioactive agents, to be separated from the beads which do not contain fluorescent targets.

Optionally, the beads containing the fluorescent targets may be further tested by adding a binding moiety known to bind to the target molecule, such as an antibody, peptide, binding partner, ligand, etc. Under certain circumstances, there may be competitive binding as between the bioactive agent and the binding moiety, with the binding moiety displacing the bioactive agent. The beads can then be resorted, and those beads which were fluorescent prior to the addition of the binding moiety but are now non-fluorescent due to the displacement of the fluorescent bioactive agent by a non-fluorescent binding partner can be collected and analyzed.

The same techniques can be used to screen multiple targets simultaneously, with each target containing a different fluorophore. Alternatively, a population of target molecules can be separated into subpopulations, with the same target molecule of each subpopulation being labelled with a different fluorophore, in order to reduce the signal for non-specific binding, i.e. only beads which contain more than one fluorophore are selected.

Once identified, the beads containing the fluorescent targets can then be treated in a variety of ways. The targets can be removed and the bioactive agent which bound to the target can be characterized structurally and biochemically, and tested in vivo, if desired, or subjected to more rigorous biochemical and functional screens. The bioactive agent may be further modified to increase affinity or specificity, elucidate functional mechanisms or binding areas, etc.

In addition, beads which did not bind targets (as well as beads that did bind targets) can be subjected to further solid phase synthesis. That is, the present methods allow the screening of combinatorial libraries as they are synthesized, at the end of each step, thus eliminating the requirement for a defined "end point" of synthesis.

Furthermore, a distinct advantage of the present invention is that the beads containing the libraries are reusable, and may be screened against any number of targets without requiring new synthesis of the candidate compounds.

Accordingly, the present invention provides methods for screening candidate bioactive agents for binding to a target molecule. By "candidate bioactive agent" or "candidate drugs" or grammatical equivalents herein is meant any molecule, e.g. proteins (which herein includes proteins, polypeptides, and peptides), small organic or inorganic molecules, polysaccharides, polynucleotides, etc. which are to be tested against a particular target. Candidate agents encompass numerous chemical classes. In a preferred embodiment, the candidate agents are organic molecules, particularly small organic molecules, comprising functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more chemical functional groups.

Candidate agents are obtained from a wide variety of sources, as will be appreciated by those in the art, including libraries of synthetic or natural compounds. As will be appreciated by those in the art, the present invention provides a rapid and easy method for screening any library of candidate agents, including the wide variety of known combinatorial chemistry-type libraries.

In a preferred embodiment, candidate agents are synthetic compounds. Any number of techniques are available for the random and directed synthesis of a wide variety of organic compounds and biomolecules, including expression of randomized oligonucleotides. See for example WO 94/24314, hereby expressly incorporated by reference, which discusses methods for generating new compounds, including random chemistry methods as well as enzymatic methods. As described in WO 94/24314, one of the advantages of the present method is that it is not necessary to characterize the candidate bioactive agents prior to the assay; only candidate agents that bind to the target need be identified. In addition, as is known in the art, coding tags using split synthesis reactions may be done, to essentially identify the chemical moieties on the beads.

Alternatively, a preferred embodiment utilizes libraries of natural compounds in the form of bacterial, fungal, plant and animal extracts that are available or readily produced, and can be attached to beads as is generally known in the art.

Additionally, natural or synthetically produced libraries and compounds are readily modified through conventional chemical, physical and biochemical means. Known pharmacological agents may be subjected to directed or random chemical modifications, including enzymatic modifications, to produce structural analogs.

In a preferred embodiment, candidate bioactive agents include proteins, nucleic acids, and chemical moieties.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occurring proteins or fragments of naturally occurring proteins. Thus, for example, cellular extracts containing proteins, or random or directed digests of proteinaceous cellular extracts, may be attached to beads as is more fully described below. In this way libraries of procaryotic and eucaryotic proteins may be made for screening against any number of targets. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 2 to about 50 amino acids, with from about 5 to about 30 amino acids being preferred, and from about 8 to about 20 being particularly preferred. The peptides may be digests of naturally occuring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

The library should provide a sufficiently structurally diverse population of randomized agents to effect a probabilistically sufficient range of diversity to allow binding to a particular target. Accordingly, an interaction library must be large enough so that at least one of its members will have a structure that gives it affinity for the target. Although it is difficult to gauge the required absolute size of an interaction library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bias is towards peptides or nucleic acids that interact with known classes of molecules. For example, when the candidate bioactive agent is a peptide, it is known that much of intracellular signaling is carried out via short regions of polypeptides interacting with other polypeptides through small peptide domains. For instance, a short region from the HIV-1 envelope cytoplasmic domain has been previously shown to block the action of cellular calmodulin. Regions of the Fas cytoplasmic domain, which shows homology to the mastoparan toxin from Wasps, can be limited to a short peptide region with death-inducing apoptotic or G protein inducing functions. Magainin, a natural peptide derived from Xenopus, can have potent anti-tumour and anti-microbial activity. Short peptide fragments of a protein kinase C isozyme (βPKC), have been shown to block nuclear translocation of βPKC in Xenopus oocytes following stimulation. And, short SH-3 target peptides have been used as psuedosubstrates for specific binding to SH-3 proteins. This is of course a short list of available peptides with biological activity, as the literature is dense in this area. Thus, there is much precedent for the potential of small peptides to have activity on intracellular signaling cascades. In addition, agonists and antagonists of any number of molecules may be used as the basis of biased randomization of candidate bioactive agents as well.

Thus, a number of molecules or protein domains are suitable as starting points for the generation of biased randomized candidate bioactive agents. A large number of small molecule domains are known, that confer a common function, structure or affinity. In addition, as is appreciated in the art, areas of weak amino acid homology may have strong structural homology. A number of these molecules, domains, and/or corresponding consensus sequences, are known, including, but are not limited to, SH-2 domains, SH-3 domains, Pleckstrin, death domains, protease cleavage/recognition sites, enzyme inhibitors, enzyme substrates, Traf, etc. Similarly, there are a number of known nucleic acid binding proteins containing domains suitable for use in the invention. For example, leucine zipper consensus sequences are known.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp169–176). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occuring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As used herein, the term "nucleoside" includes nucleotides and nucleoside and nucleotide analogs, and modified nucleosides such as amino modified nucleosides. In addition, "nucleoside" includes non-naturally occuring analog structures. Thus for example the individual units of a peptide nucleic acid, each containing a base, are referred to herein as a nucleoside.

As described above generally for proteins, nucleic acid candidate bioactive agents may be naturally occuring nucleic acids, random nucleic acids, or "biased" random nucleic acids. For example, digests of procaryotic or eucaryotic genomes may be used as is outlined above for proteins. Where the ultimate expression product is a nucleic acid, at least 10, preferably at least 12, more preferably at least 15, most preferably at least 21 nucleotide positions need to be randomized, with more preferable if the randomization is less than perfect. Similarly, at least 5, preferably at least 6, more preferably at least 7 amino acid positions need to be randomized; again, more are preferable if the randomization is less than perfect.

In a preferred embodiment, the candidate bioactive agents are organic moieties. In this embodiment, as is generally described in WO 94/24314, candidate agents are synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracylines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or candidate agents which can then be tested using the present invention.

As will be appreciated by those in the art, it is possible to screen more than one type of candidate agent at a time. Thus, the library of candidate agents used in any particular assay may include only one type of agent (i.e. peptides), or multiple types (peptides and organic agents).

The candidate bioactive agents are covalently attached to beads. By "beads" or "particles" or "solid supports" or "microspheres" or grammatical equivalents herein is meant small discrete particles, preferably but not required to be roughly spherical, generally of about 3 to about 200 $\mu$m in diameter. The composition of the beads will vary, depending on the class of candidate bioactive agent and the method of synthesis. Suitable bead compositions include those used in peptide, nucleic acid and organic moiety synthesis, including, but not limited to, glass, polymers such as polystyrene, latex or cross-linked dextrans such as Sepharose, cellulose, nylon, teflon, TentaGel, etc.

In a preferred embodiment, the beads may be labeled, either with a fluorescent label, or preferably another type of label, for example, binary tags that allow the subsequent identification of the agent on the bead; see Maclean et al., PNAS USA 94:2805 (1997); Ni et al., J. Med. Chem. 39:1601 (1996); Ni et al., Methods in Enzymol. 267:261 (1996); and Gallop, Chemtracts-Organic Chemistry 7:172 (1994), all of which are incorporated by reference.

As is generally described herein, the candidate bioactive agents may either be synthesized directly on the beads, or they may be made and then attached after synthesis.

In a preferred embodiment, the candidate agents are synthesized directly on the beads. As is known in the art, many classes of chemical compounds are currently synthesized on solid supports, such as peptides, organic moieties, and nucleic acids. It is a relatively trivial matter to adjust the current synthetic techniques to use beads. As will be appreciated by those in the art, the literature contains numerous examples of the synthesis of candidate agents (particularly libraries of candidate agents on solid-phase supports; see for example Pavia et al. Bioorganic & Medicinal Chemistry 1996 4(5):659–666; Liskamp et al., Bioorganic & Medicinal Chemistry 1996 4(5):667–672; Tong et al., Bioorganic & Medicinal Chemistry 1996 4(5):693–698; Houghten et al., Bioorganic & Medicinal Chemistry 1996 4(5):709–715, Freier et al., Bioorganic & Medicinal Chemistry 1996 4(5):717–725; Bolton et al., Tetrahedron Letters 1996 37(20) 3433–3436, all of which are hereby expressly incorporated by reference).

In a preferred embodiment, it may be desirable to use linkers to attach the candidate agents to the beads, to allow both good attachment, sufficient flexibility to allow good interaction with the target molecule, and to avoid undesirable binding reactions. See Yu et al., Bioorganic & Medicinal Chemistry Letters 1997 7(1) 95–98; Wennemers et al., Tett. Lett. p6413 (1994), both of which are incorporated by reference.

One advantage of the present invention is that it allows the screening of intermediates in a synthetic pathway. That is, when the candidate agents are synthesized on the beads, it is possible to screen the beads at any point during the synthesis. Thus for example, the initial chemical unit or substrate is attached to the beads, and a first chemical modification reaction is done, to form a set of derivatives different from the starting set. Chemical modification in this context includes both chemical or enzymatic reactions. These reactions can generally be categorized into classes by the number of substrate and products. Thus, a first class transforms a single substrate into a single product; for example, an isomerization reaction. A second class joins two or more substrates to form one product; a dehydration reaction joining two nucleotides by an ester bond is an example. A third class cleaves one substrate into two or more products; for example, the cleavage of a protein by a protease. A fourth class transforms two substrates into two products, for example by the transfer of a reactive group from one substrate to another. All of these chemical modification reactions can be the result of chemical reactions or enzymatic ones, with "enzymatic" in this context including the use of naturally or non-naturally occuring enzymes, as well as other catalysts (such as catalytic surfaces or metal ligands).

The new moieties (i.e. starting materials after a chemical modification) are then tested as candidate bioactive agents using the methods of the present invention. Additional reactions can then be done, and the beads retested. As will be appreciated by those in the art, in some embodiments it may be useful to remove any beads that contain bioactive agents that bind the target molecules, and only do additional synthetic reaction steps on candidate agents that do not bind the target. Alternatively, it may be desirable to modify bioactive agents that do bind the target molecule in order to generate bioactive agents that bind to the target with a higher affinity, or to a related target, etc. In this embodiment, any bound target molecules must be removed prior to further chemical modification. Thus, the present invention provides a rapid and easy way of screening intermediates in a given synthetic pathway.

In a preferred embodiment, the candidate agents are synthesized first, and then covalently attached to the beads. As will be appreciated by those in the art, this will be done depending on the composition of the candidate agents and the beads. The functionalization of solid support surfaces such as certain polymers with chemically reactive groups such as thiols, amines, carboxyls, etc. is generally known in the art. Generally, the candidate agents are attached using functional groups on the candidate agent. For example, candidate agents containing carbohydrates may be attached to an amino-functionalized support; the aldehyde of the carbohydrate is made using standard techniques, and then the aldehyde is reacted with an amino group on the surface. In an alternative embodiment, a sulfhydryl linker may be used. There are a number of sulfhydryl reactive linkers known in the art such as SPDP, maleimides, a-haloacetyls, and pyridyl disulfides (see for example the 1994 Pierce Chemical Company catalog, technical section on cross-linkers, pages 155–200, incorporated herein by reference) which can be used to attach cysteine containing proteinaceous agents to the support. Alternatively, an amino group on the candidate agent may be used for attachment to an amino group on the surface. For example, a large number of stable bifunctional groups are well known in the art, including homobifunctional and heterobifunctional linkers (see Pierce Catalog and Handbook, pages 155–200). In an additional embodiment, carboxy groups (either from the surface or from the candidate agent) may be derivatized using well known linkers (see the Pierce catalog). For example, carbodiimides activate carboxy groups for attack by good nucleophiles such as amines (see Torchilin et al., *Critical Rev. Therapeutic Drug Carrier Systems*, 7(4):275–308 (1991), expressly incorporated herein). Similarly, a number of homo- and heterobifunctional agents are known for amine-amine crosslinking, thiol-thiol crosslinking, amine-thiol crosslinking, amine-carboxylic acid crosslinking, and carbohydrate crosslinking to amines and thiols; see Molecular Probes Catalog, 1996, Sixth Edition, chapter 5, hereby incorporated by reference. In addition, proteinaceous candidate agents may also be attached using other techniques known in the art, for example for the attachment of antibodies to polymers; see Slinkin et al., *Bioconj. Chem.* 2:342–348 (1991); Torchilin et al., supra; Trubetskoy et al., *Bioconj. Chem.* 3:323–327 (1992); King et al., *Cancer Res.* 54:6176-6185 (1994); and Wilbur et al., *Bioconjugate Chem.* 5:220–235 (1994), all of which are hereby expressly incorporated by reference). It should be understood that the candidate agents may be attached in a variety of ways, including those listed above. What is important is that manner of attachment does not significantly alter the functionality of the candidate agent; that is, the candidate agent should be attached in such a flexible manner as to allow its interaction with a target.

In general, it is desirable to have a library of candidate agents attached to beads. By "library of candidate agents" herein is meant generally at least about $10^2$ different compounds, with at least about $10^3$ different compounds being preferred, and at least about $10^4$, $10^5$ or $10^6$ different compounds being particularly preferred.

In general, it is preferred that each bead contain a multiplicity of candidate agents. That is, each bead will contain at least about 10 candidate agents, with at least about 100 being preferred, and at least about 1000 being especially preferred.

As will be appreciated by those in the art, each bead may contain one type of candidate agent, or more than one. That is, in a preferred embodiment, any single bead contains a single type of candidate bioactive agent. This may be preferred for a variety of reasons, including synthetic considerations, ease of characterization of downstream "hits", and fluorescent detection limits (that is, the number of fluorescent targets that should be bound to a bead to allow FACS sorting).

Alternatively, (for example when libraries of naturally occuring compounds are attached to beads), each bead may contain more than one type of candidate agent. In this embodiment, as is more fully outlined herein, it will generally be desirable to "amplify" the fluorescent signal (i.e. have more than one fluorescent label per target) to facilitate detection.

In a preferred embodiment, there are a number of beads that each contain a single candidate agent. That is, there are a number of beads each containing a particular candidate agent. Thus, at least about 100 beads per candidate agent are used, with at least about 1000 being preferred and at least about 10,000 to 100,000 being especially preferred.

Thus, the library of candidate bioactive agents are contained upon a plurality of beads.

Once generated, the library of beads containing a library of covalently attached candidate agents is added to at least a first population of a first target molecule. By "target molecule" herein is meant a molecule for which an interaction is sought; this term will be generally understood by those in the art. Suitable target molecules include, but are not limited to, proteins such as receptors, enzymes, cell-surface receptors, G-protein coupled receptors, ion channels, transport proteins, transcription factors, vesicle proteins, adhesion proteins, etc.

The target molecule comprises a first labeling moiety. Either the first labeling moiety comprises a fluorescent label, or a second labeling moiety is used, that is fluorescent and will bind to the first labeling moiety.

In a preferred embodiment, the first labeling moiety comprises at least a first fluorescent label. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Suitable optical dyes are described in the 1996 Molecular Probes Handbook by Richard P. Haugland, hereby expressly incorporated by reference.

In a preferred embodiment, the fluorescent label is functionalized to facilitate covalent attachment, as is generally outlined above for the attachment of candidate agents to surfaces. Thus, a wide variety of fluorescent labels are commercially available which contain functional groups, including, but not limited to, isothiocyanate groups, amino groups, haloacetyl groups, maleimides, succinimidyl esters, and sulfonyl halides, all of which may be used to covalently attach the fluorescent label to a second molecule, as is described herein. The choice of the functional group of the fluorescent label will depend on the site of attachment to either a linker, as outlined below, the first labeling moiety, the target molecule, or the second labeling moiety.

The covalent attachment of the fluorescent label may be either direct or via a linker. In one embodiment, the linker is a relatively short coupling moiety, that is used to attach the molecules. A coupling moiety may be synthesized directly onto a candidate agent for example, and contains at least one functional group to facilitate attachment of the fluorescent label. Alternatively, the coupling moiety may have at least two functional groups, which are used to attach a functionalized candidate agent to a functionalized fluorescent label, for example. In an additional embodiment, the linker is a polymer. In this embodiment, covalent attachment is accomplished either directly, or through the use of coupling moieties from the agent or label to the polymer. In a preferred embodiment, the covalent attachment is direct, that is, no linker is used. In this embodiment, the candidate agent preferably contains a functional group such as a carboxylic acid which is used for direct attachment to the functionalized fluorescent label. Thus, for example, for direct linkage to a carboxylic acid group of a candidate agent, amino modified or hydrazine modified fluorescent labels will be used for coupling via carbodiimide chemistry, for example using 1-ethyl-3-(3-dimethylaminopropyl)-carbodiimide (EDC) as is known in the art (see Set 9 and Set 11 of the Molecular Probes Catalog, supra; see also the Pierce 1994 Catalog and Handbook, pages T-155 to T-200, both of which are hereby incorporated by reference). In one embodiment, the carbodiimide is first attached to the fluorescent label, such as is commercially available.

Thus, in a preferred embodiment, a fluorescent label is attached, either directly or via a linker, to the candidate agents and thus serves as a first labeling moiety. Alternatively, in a preferred embodiment, the first labeling moiety comprises a first partner of a binding pair, which may or may not be fluorescent, and a second labeling moiety, comprising the second partner of a binding pair, and at least one fluorescent label, as defined above.

Suitable binding pairs include, but are not limited to, antigens/antibodies, including digoxigenin/antibody, dinitrophenyl (DNP)/anti-DNP, dansyl-X/anti-dansyl, fluorescein/anti-fluorescein, lucifer yellow/anti-lucifer yellow, rhodamine/anti-rhodamine; and biotin/avidin (or biotin/strepavidin). Preferred binding pairs (i.e. first and second labeling moieties) generally have high affinities for each other, sufficient to withstand the shear forces during FACS sorting.

Generally, in a preferred embodiment, the smaller of the binding partners serves as the first labeling moiety, as steric considerations in agent:target binding may be important. Thus, preferred first labeling moieties (when second labeling moieties are used), include, but are not limited to, haptens such as biotin, etc. Biotinylation of target molecules is well known, for example, a large number of biotinylation agents are known, including amine-reactive and thiol-reactive agents, for the biotinylation of proteins, nucleic acids, carbohydrates, carboxylic acids; see chapter 4, Molecular Probes Catalog, Haugland, 6th Ed. 1996, hereby incorporated by reference. Similarly, a large number of haptenylation reagents are also known; supra.

In this embodiment, attachment of the first labeling moiety to the candidate agents will be done as is generally appreciated by those in the art, and may include techniques outlined above for the incorporation of fluorescent labels.

In this embodiment, a second labeling moiety that comprises at least a first fluorescent label is used. The fluorescent labels are generally attached as outlined above. The second labeling moiety, i.e. the other partner of the binding pair, has at least one fluorescent label, with at least 5 being preferred and at least 10 being particularly preferred. This is determined on the basis of the sensitivity of the FACS sorting. In general, 10 to 100 fluores per sorting event are needed; i.e. per bead, with from about 20 to 100 being preferred, and from 30 to 90 being especially preferred. This can be accomplished by amplifying the signal per target, i.e. have each second label comprise multiple fluores, or by having a high density of target binding per bead; or a combination of both. Thus, in some situations, binding of ten targets to a single bead, each containing at least one to 10 fluores may be done.

In a preferred embodiment, all the target molecules contain the same fluorescent label (that is, all of either the first or the second labeling moieties comprise a single type of fluorescent label). In an alternative embodiment, the target molecule population is divided into at least two subpopulations, each comprising a different fluorescent label. This may be particularly preferred to reduce false positives; that is, only beads comprising both labels (i.e. beads with a single candidate agent type that bind targets with both labels) will constitute "real" interactions. In a preferred embodiment, up to four different labels may be used in the current FACS systems, with eight being possible soon.

In one embodiment, the target molecules are also bound to beads. In a preferred embodiment, the target molecules are attached to the beads using preferably flexible linkers, to allow for interaction with bead-bound agents. In this embodiment, a preferred system utilizes fluorescent beads; that is, the bead to which the target molecules is attached can be fluorescent, thus serving as the first or second labeling moiety. See for example the Molecular Probes catalog, supra, chapter 6, hereby incorporated by reference.

The beads containing the candidate agents are added to the target molecules under reaction conditions that favor agent-target interactions. Generally, this will be physiological conditions. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away.

A variety of other reagents may be included in the assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

In a preferred embodiment, the beads containing the candidate agents are added to a single target molecule population, i.e. where the target molecules are all the same. In an additional preferred embodiment, the beads can be added to more than one target molecule population at a time, with each target molecule preferably containing, although it is not required, a different fluorescent label.

In a preferred embodiment, the target molecules comprising the first labeling moieties are added first, and allowed to react under favorable binding conditions for a period of time. The beads are then removed from the reaction mixture, optionally but preferably washed or rinsed one or more times to remove excess reagents including target molecules, and either sorted, or the second labeling moiety, if used, is added. Washing or rinsing the beads will be done as will be appreciated by those in the art, and may include the use of filtration, centrifugation, the application of a magnetic field, electrostatic interactions for charged beads, adhesion, etc. When second labeling moieties are used, they are preferably added after excess non-bound target molecules are removed, in order to reduce non-specific binding; however, under some circumstances, all the components may be added simultaneously.

The beads are then sorted using fluorescent-activated cell sorting (FACS). In general, $K_D$s of $\leq 1$ μM are preferred, to allow for retention of binding in the presence of the shear forces present in FACS sorting. In a preferred embodiment, the beads are sorted at very high speeds, for example greater than about 5,000 sorting events per sec, with greater than about 10,000 sorting events per sec being preferred, and greater than about 25,000 sorting events per second being particularly preferred, with speeds of greater than about 50,000 to 100,000 being especially preferred.

The sorting results in a population of non-fluorescent beads and at least one population of fluorescent beads, depending on how many fluorescent labels were used. The presence of at least one fluorescent bead is indicative that at least one candidate bioactive agent is a bioactive agent that binds to the target molecule.

Once a fluorescent bead, i.e. a bead containing at least one bioactive agent that is bound to the target, is isolated, a number of things may be done.

In a preferred embodiment, the characterization of the bioactive agent is done. This will proceed as will be appreciated by those in the art, and generally includes an analysis of the structure, identity, binding affinity and function of the agent.

In one embodiment, the candidate agent is attached to the bead in such a manner as to allow subsequent cleavage. Thus, in this embodiment, the candidate agent may be cleaved off and analyzed, for example via mass spectroscopy, to elucidate the structure of the bioactive agent. Alternatively, binary tags such as those outlined above may be used.

Generally, once identified, the bioactive agent is resynthesized and combined with the target molecule to verify the binding. In addition, once binding bioactive agents are found, they may be tested in functional screens to determine their effect on the target molecule. These functional screens will be done depending on the target molecule, as will be appreciated by those in the art.

In a preferred embodiment, either the non-reactive beads (i.e. the non-fluorescent beads), or the fluorescent beads (to which fluorescent target is bound), or both, can be subjected to altered experimental conditions and resorted. This may be done, for example, to quantify or alter the binding affinity of the bioactive agent for the target. Thus, for example, changes in pH, temperature, buffer or salt concentration, etc. In a preferred embodiment, the pH is changed, generally by increasing or decreasing the pH, usually by from about 0.5 to about 3 pH units. Alternatively, the temperature is altered, with increases or decreases of from about 5° C. to about 30° C. being preferred. Similarly, the salt concentration may be modified, with increases or decreases of from about 0.1 M to about 2 M being preferred.

In a preferred embodiment, either the non-reactive beads (i.e. the non-fluorescent beads), or the fluorescent beads (to which fluorescent target is bound), or both, can be treated such that further chemical modifications are done. As outlined herein, the present invention is useful to test the products from each chemical step in a synthetic reaction against one or more target molecules, for example in combinatorial chemical library synthesis. Thus, at any point in a synthetic scheme, beads containing the products maybe tested using the present methods. This may require the washing or buffer exchange of the beads as is outlined herein. The beads are sorted, and either or both of the fluorescent and non-fluorescent beads may be returned to a reaction vessel for further chemical modifications, as outlined above.

In a preferred embodiment, the affinity and specificity of the binding reaction may be tested using a known binding agent, i.e. a competitor. Thus generally, the population of fluorescent beads (i.e. beads to which a fluorescent target is bound), is subjected to further steps. A binding molecule is added to the fluorescent beads. By "binding molecule" or "competitor moiety" or grammatical equivalents herein is meant a molecule known to bind to the target molecule, including, but not limited to, antibodies, peptides and nucleic acids.

In a preferred embodiment, the competitor is also labeled, preferably with a different fluorescent label than the target. This will allow the detection of binding agents that either bind to the same binding site as the competitor (in which case only one label will be detected), or that bind to a different binding site than the competitor (in which case two labels should be detected).

In a preferred embodiment, either the non-reactive beads (i.e. the non-fluorescent beads), or the fluorescent beads (to which fluorescent target is bound), or both, can be added to a second population of second target molecules. As is outlined herein, this may be done either simultaneously with the first target molecule population or sequentially. In a preferred embodiment, particularly when two target molecules are analyzed at the same time, the second target molecule utilizes a different fluorescent label than the first target molecule, although this is not required. Additionally embodiments utilize third, fourth, etc. populations of target molecules.

As will be appreciated by those in the art, the ability to reuse the candidate agent library, on the beads, is a significant advantage. As will be appreciated by those in the art, when sequential analysis is done, it is preferable to remove any bound target molecules from the beads, for example by increasing the salt concentration, pH or temperature, or by adding a competitor, to remove any target molecules bound to the beads. All references cited herein are incorporated by reference.

I claim:

1. A method for screening bioactive agents which bind to a target molecule, while reducing the incidence of false positives, said method comprising:
   (a) providing a population of one species of target molecule comprising at least a first subpopulation labeled with a first fluorescent moiety and a second subpopulation labeled with a second fluorescent moiety, wherein the target molecules in the first and second subpopulations are the same;
   (b) contacting a library of candidate bioactive agents covalently attached to a plurality of beads with said population of target molecules under reaction conditions that favor binding of the target molecule to a member of said library of bioactive agents; and
   (c) sorting the beads from step (b) using a fluorescent activated cell sorter (FACS) machine to obtain a fluorescent population of beads and a non-fluorescent population of beads, wherein the beads in said fluorescent population have said first and second fluorescent moieties bound thereto, thereby indicating the binding of said target molecule to at least one member of said library of candidate bioactive agents.

2. The method according to claim 1 further comprising:
   (d) identifying member(s) of said library that bound to said population of target molecule.

3. The method according to claim 1, wherein said candidate bioactive agents are synthesized on said plurality of beads.

4. The method according to claim 1, wherein said target molecule is located on a cell and said cell is contacted with said library of candidate bioactive agents.

* * * * *